US009283138B1

(12) United States Patent
Rosenblum (10) Patent No.: US 9,283,138 B1
(45) Date of Patent: Mar. 15, 2016

(54) COMMUNICATION TECHNIQUES AND DEVICES FOR MASSAGE THERAPY (71) Applicant: Keith Rosenblum, Minneapolis, MN (US)

(72) Inventor: Keith Rosenblum, Minneapolis, MN (US)

(73) Assignee: Keith Rosenblum, Minneapolis, MN (US)

(*) Notice: Subject to any disclaimer, the term of this patent is extended or adjusted under 35 U.S.C. 154(b) by 0 days.

(21) Appl. No.: 14/522,953

(22) Filed: Oct. 24, 2014

(51) Int. Cl.
*A61H 1/00* (2006.01)
*A61H 23/00* (2006.01)

(52) U.S. Cl.
CPC ........ *A61H 23/00* (2013.01); *A61H 2201/5023* (2013.01); *A61H 2201/5038* (2013.01); *A61H 2201/5043* (2013.01)

(58) Field of Classification Search
CPC .................. A61H 2201/50; A61H 2201/5002; A61H 2201/5007; A61H 2201/501; A61H 2201/5012; A61H 2201/5023; A61H 2201/5035; A61H 2201/5033; A61H 2201/5038; A61H 2201/5043; A61H 23/00
See application file for complete search history.

(56) References Cited

U.S. PATENT DOCUMENTS

| 4,905,001 | A | 2/1990 | Penner |
| 6,368,268 | B1 * | 4/2002 | Sandvick et al. ............... 600/38 |
| 6,585,668 | B2 | 7/2003 | Nissim |
| 7,236,574 | B2 | 6/2007 | Haldeman et al. |
| 7,356,473 | B2 | 4/2008 | Kates |
| 7,517,327 | B1 | 4/2009 | Knight |
| 7,608,037 | B2 * | 10/2009 | Levy ............................... 600/38 |
| 7,889,187 | B2 | 2/2011 | Freier et al. |
| 8,280,954 | B2 | 10/2012 | Curry et al. |
| 8,350,843 | B2 | 1/2013 | Rogowitz et al. |
| 8,508,469 | B1 | 8/2013 | Rosenberg et al. |
| 2001/0042962 | A1 | 11/2001 | Simmons |
| 2003/0212352 | A1 | 11/2003 | Kahn |
| 2004/0082831 | A1 * | 4/2004 | Kobashikawa et al. ......... 600/38 |
| 2004/0098256 | A1 | 5/2004 | Nissen |
| 2005/0086699 | A1 | 4/2005 | Hahn et al. |
| 2006/0026001 | A1 | 2/2006 | Bravin et al. |
| 2006/0074624 | A1 | 4/2006 | Sahashi |
| 2006/0125914 | A1 | 6/2006 | Sahashi |
| 2008/0259056 | A1 | 10/2008 | Freier et al. |
| 2009/0164458 | A1 | 6/2009 | Jung et al. |
| 2010/0261530 | A1 | 10/2010 | Thomas et al. |
| 2011/0004048 | A1 | 1/2011 | Brunelle |
| 2012/0259927 | A1 | 10/2012 | Lockhart |
| 2013/0079061 | A1 | 3/2013 | Jadhav et al. |

(Continued)

FOREIGN PATENT DOCUMENTS

| WO | WO-0197206 | A1 | 12/2001 |
| WO | WO-03105059 | A1 | 12/2003 |

(Continued)

*Primary Examiner* — Quang D Thanh
(74) *Attorney, Agent, or Firm* — Schwegman Lundberg & Woessner, P.A.

(57) ABSTRACT

A system to convey massage preferences of a first user to a second user, the first user to receive a massage from the second user, the system comprising a first interactive device, including an input module for receiving a set of preference inputs from the first user, the set of preference inputs describing a massage to be received by the first user, a process module for processing the set of preference inputs, and a transmission module for transmitting a representation of the set of preference inputs to a second interactive device, where the second interactive device includes an interface for displaying the representation of the set of preference inputs to a second user.

17 Claims, 7 Drawing Sheets

(56) References Cited

U.S. PATENT DOCUMENTS

| | | |
|---|---|---|
| 2013/0115579 A1 | 5/2013 | Taghavi |
| 2013/0198625 A1* | 8/2013 | Anderson et al. ............. 715/701 |
| 2013/0286446 A1 | 10/2013 | Nitta |
| 2015/0119771 A1* | 4/2015 | Roberts ......................... 601/135 |

FOREIGN PATENT DOCUMENTS

| | | |
|---|---|---|
| WO | WO-2011031241 A1 | 3/2011 |
| WO | WO-2013049248 A2 | 4/2013 |

\* cited by examiner

COMMUNICATION TECHNIQUES AND DEVICES FOR MASSAGE THERAPY

TECHNICAL FIELD

Embodiments described herein generally relate to communications between a massage professional and a massage patient and in particular, to communications during a massage session.

BACKGROUND

Massage therapy involves the manual manipulation of superficial and deep tissue to achieve a beneficial effect for a patient. Relaxation massage, such as Swedish massage, is suggested to increase oxygen levels and circulation of blood in a massage patient and generally enhance the overall well-being of the massage patient. Therapeutic massage, such as myofacial release, can be used to improve the flexibility of the tissues in a massage patient for relieving pain and reducing stress to improve patient health.

Existing communication practices of therapeutic massage typically involve verbal instruction and feedback exchanged between a massage patient and a massage professional (e.g., a masseur/masseuse) during the therapeutic massage session. For example, the massage patient may verbally describe the desired therapeutic massage to the massage professional prior to the therapeutic massage. Further, the massage patient may inform the massage professional about the amount of pain experienced as the therapeutic massage is applied to a particular area of the body so that the massage professional can adjust the therapeutic massage to improve the comfort of the massage patient.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The amount of communication that occurs between a massage professional and a massage patient can vary depending on the goals of the massage and the type of massage applied. For example, in relaxation massage, a massage patient may desire to minimize external stimulus, such as verbal communication, to enhance a meditative state that can be induced during the massage. In therapeutic massage, the massage patient may be in active communication with the massage professional to provide feedback on the comfort and effectiveness of the therapeutic massage delivered, yet still desire to minimize verbal communication to enhance the meditative state that can be induced during the massage.

The following disclosure describes systems, techniques, and configurations that facilitate the capture, process, and display of communications between a massage patient and a massage professional via the use of interactive devices. In an example, the systems, techniques, and configurations allow a massage patient to communicate silently with a massage professional contemporaneously during a massage session to minimize external stimulus and disturbances while enhancing any massage-induced meditative state of the massage patient. In other examples, the systems, techniques, and configurations described herein allow a massage patient to select or modify preferences inputs before and after a massage session for review by and communication with the massage professional or other interested parties. In further examples, the techniques and configurations described herein record, monitor, and track patient preferences and professional activities that occur (or are scheduled to occur) during the therapeutic massage session.

Preference inputs serve to characterize aspects of the therapeutic massage. Examples of preference inputs include, but are not limited to, primary preference inputs, such as body zones (e.g., parts of the body to be massaged), and secondary preference inputs, such as massage intensity (e.g., the level of force applied to the body zone) and massage duration (e.g., the length of time massage is applied to the body zone). Secondary preference inputs can serve to further characterize primary preference inputs. In an example, a therapeutic massage session can be defined by one or more primary preference inputs, such as the body zone and each primary preference input can be further described by one or more secondary preference inputs, such as massage intensity and massage duration. For example, a massage patient can specify a primary preference input for massage, such as the shoulders, and secondary preference inputs associated with the primary preference input, such as the massage intensity or the massage duration applied to the shoulders.

As used herein, the term "body zone" can include any grouping of contiguous or non-contiguous muscle groups to which therapeutic massage is applied. As used herein, the term "muscle group" can include any grouping of contiguous tissue to which therapeutic massage is applied. For example, a first body zone can include the muscle groups of the head and upper neck; a second body zone can include the muscle groups of the lower neck, shoulders and arms; a third body zone can include the muscle groups of the middle back; a fourth body zone can include the muscle groups of the lower back and upper hips; a fifth body zone can include the muscle groups of the buttocks and thighs; and a sixth body zone can include the muscle groups of the shins and feet. It is understood that other groupings of contiguous tissues can be used to describe one or more muscle groups and other groupings of muscle groups can be used to describe one or more body zones.

Prior to the start of a therapeutic massage, a massage patient defines the therapeutic massage by identifying a set of preference inputs through an interface in electrical communication with a first interactive device. Examples of an interface include, but are not limited to, mechanical devices such as a buttons or switches, or electrical interfaces such as a graphical user interface (GUI). As such, a therapeutic massage can be described by one or more preference inputs.

Preference inputs are collected from the massage patient through an application ("app") running on an electronic device. The app receives preference inputs from a massage patient via an interface, processes the preference inputs, and thereafter displays the preference inputs through an interface.

A representation of the set of preference inputs is displayed to the massage professional through an interface in electrical communication with an electronic device in preparation for delivery of the therapeutic massage to the massage patient. Preparation for delivery of the therapeutic massage can include, but is not limited to, understanding the order of body zones to be massaged during the therapeutic massage, allocating time for each body zone massage, and planning on the amount of force required to deliver the requested massage intensity to each body zone.

During the therapeutic massage, the massage patient can modify one or more preference inputs of the set of preference inputs to form an updated set of preference inputs. A representation of the updated set of preference inputs is subsequently processed and displayed to the massage professional where the representation includes an alert message. An alert message is a notice to the massage patient and the massage professional that a preference input has been modified or otherwise changed.

After the therapeutic massage, the massage patient or the massage professional can save the preference inputs to a massage patient profile for use in a future therapeutic or relaxation massage.

Thus, the systems, techniques, and configurations described herein provide several advantages over other systems, including, the ability to silently or substantially silently communicate changes to a therapeutic massage while the therapeutic massage is in progress, an alert function to notify the massage professional that one or more parameters in the therapeutic massage has changed, and the ability to save, access, or save and access a massage patient profile for use in a future therapeutic massage.

Figure 1:
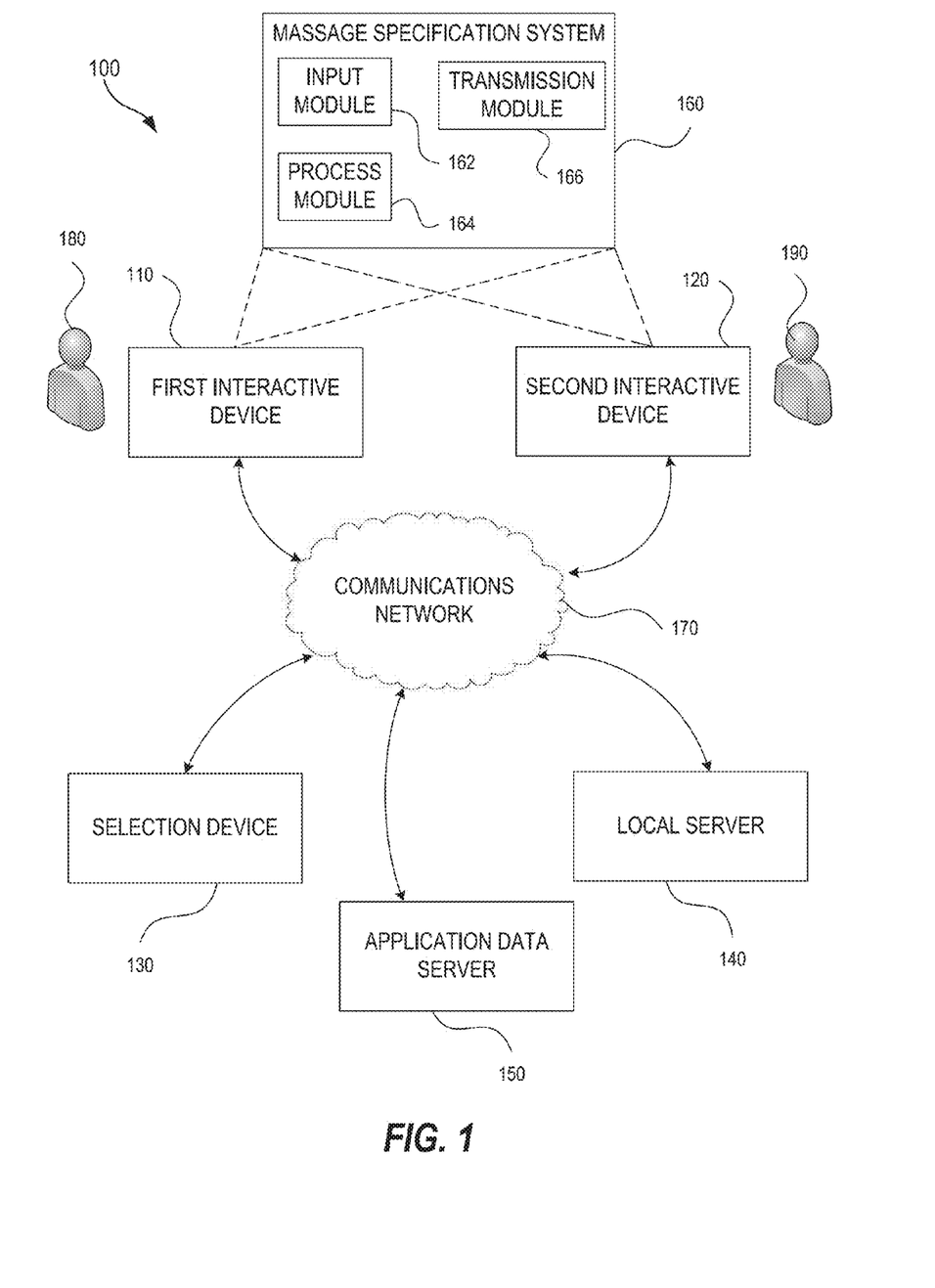
FIG. 1 is a block diagram of an electronic system configured to communicate information used in a therapeutic massage session from a first user to a second user according to an example.

FIG. 1 is a block diagram of an electronic system 100 configured to communicate information regarding a therapeutic massage from a first user 180 to a second user 190 according to an example. The term "first user" can refer to any entity that provides input data to an interactive device. For example, the first user 180 can include, but is not limited to, a patient who receives a massage (e.g., a massage patient) or any other person concerned with the patient's wellbeing, such as a medical doctor, a nurse, a caregiver, or a massage professional (e.g., a masseur). The term "second user" can refer to any entity that receives a representation of the input data from an interactive device. For example, the second user can include, but is not limited to, a person who delivers a massage to a patient, such as a massage professional. Although first and second users are described herein, it is understood that communications can be provided from the first user to any number of other users. For example, while only one first user is discussed, it is understood that preference data can be received from one or more "first users" and communicated to one or more "second users."

FIG. 1 shows a first interactive device 110, a second interactive device 120, a selection device 130, a local server 140, an application data server 150, and a massage specification system 160, each communicatively coupled via a communications network 170.

The first interactive device 110 and second interactive device 120 are instruments for communication between a first user 180 and a second user 190 during a massage. An "interactive device" can include, but is not limited to, devices that operate to receive input data through an interface, process the input data resulting in processed data, display a representation of the input data or processed data through an interface and connect to a communications network. In an example, an interactive device can include, but is not limited to, electronic devices such as mobile electronic devices (e.g., smartphones, tablet computers or portable computers) or touchscreen displays. For example, in an embodiment, the first interactive device 110 can be a cell phone and the second interactive device 120 can be a touchscreen monitor.

An "interface" can include, but is not limited to, a mechanical device such as a button or switch, or an electrical interface such as a GUI.

In operation, the first interactive device 110 receives preference inputs for processing from the first user 180 and the second interactive device 120 displays a representation of the preference inputs to the second user 190. Preference inputs relate to a set of variables pertinent to the delivery of a therapeutic massage or external medical therapy. In an example, a set of preference inputs can define a therapeutic massage. In an example, preference inputs associated with a therapeutic massage can include, but are not limited to, the parts of the body massaged, such as a body zone, the massage intensity (e.g., the level of force applied to the body zone) and the massage duration (e.g., the length of time massage is applied to the body zone).

The first user 180 uses selection device 130 for specifying preference inputs that is in communication with the first interactive device 110, the second interactive device 120, or both the first and second interactive devices 110, 120. In some examples, the selection device 130 is an electronic device with an electrical interface such as a GUI. For example, the selection device 130 can include, but is not limited to, mobile electronic devices (e.g., smartphones, tablet computers or portable computers) or touchscreen displays. In some examples, the selection device 130 is an electronic device with a mechanical interface such as a button or switch. For example, the selection device 130 can include, but is not limited to, a computer mouse, a joystick, a touchpad, or any similar peripheral or input mechanism that can be used to control, select, or activate objects on a graphical user interface. In some examples, the selection device 130 is a non-contact selection interface, or an interface that does not require physical contact of the selection device 130 by the user to make a preference input selection. For example, the non-contact selection interface can include, but is not limited to, gesture-interpreting interfaces, eye tracking interfaces, brainwave interfaces or any similar peripheral or input mechanism that can be used to control, select, or activate objects on a graphical user interface.

Figure 2:
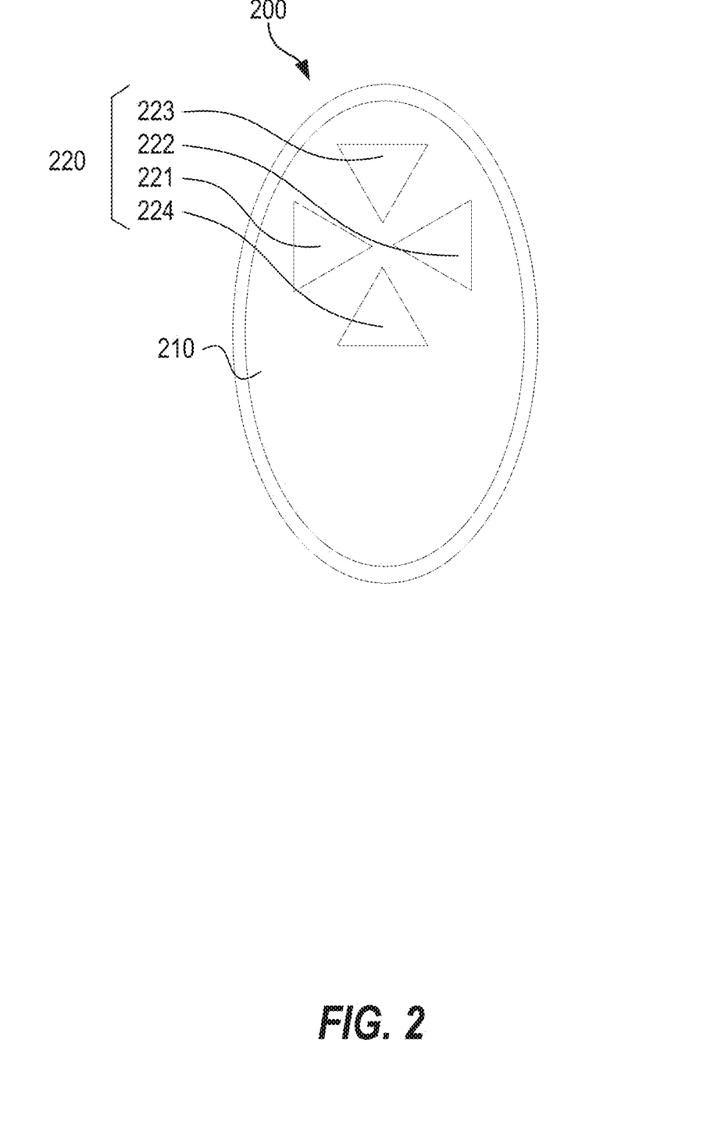
FIG. 2 is an illustration of an example selection device.

FIG. 2 is an illustration of an example selection device 200. In an example, the selection device 200 is an electronic device with a mechanical interface. For example, the selection device 200 can include a body 210, one or more selection controls 220, and electronic circuits (not shown).

The body 210 is configured to support the one or more selection controls 220 and to enclose and protect the electronic circuits from the environment in which the selection device 200 is used. In an example, the body 210 can be constructed from a single, continuous segment of material or two or more segments of material. For example, the body 210 can include two shell-like structures configured to reversibly engage one another to form a single contiguous structure such that electronic circuits housed within the body 210 are protected from the environment. In an example, the body 210 is configured to be supported in the hand of a user so that at least one selection control 220 can be activated by at least one finger on the hand of the user supporting the selection device 200.

The selection controls 220 are activated by the first user 180 or second user 190 to select or control objects on a graphical user interface, or GUI. The selection controls 220 can include a mechanical interface, such as a button, a switch, or a toggle, or an electronic interface, such as a GUI. FIG. 2 shows an example where the selection control 220 includes four selection buttons 221, 222, 223 and 224. In an example, the four section buttons 221, 222, 223 and 224 are configured to modify the secondary preference inputs of a primary preference input. For example, the selection button 221 can increase the massage intensity, the selection button 222 can decrease the massage intensity, the selection button 223 can increase the massage duration, and the selection button 224 can decrease the massage duration.

The electronic circuits are configured to convert activation of the selection controls 220 to corresponding control or motion of an icon object on a GUI. In an example, as a user activates the selection controls 220, the electronic circuits cause the icon object to move from a first location to a second location on the GUI. In an example, the electronic circuits include network interfaces for communication with other components of the system 100 and one or more electrical sources, such as batteries, to power the selection device 200.

Returning to FIG. 1, the local server 140 and the application data server 150 include a processor, display, network interface, memory, one or more applications stored on the memory, and an input interface. Input interfaces may include touchscreens, a keyboard, a stylus, gesture control, or voice control. Network interfaces include interfaces capable of receiving and sending data such as wireless interfaces CDMA, GSM, Wi-Fi, WiMAX, or wired interface such as Ethernet or USB. The processor executed instructions stored on the memory to provide functionality as described herein. In various embodiments, the local server 140 and the application data server 150 are personal computers. In various embodiments, the local server 140 and the application data server 150 are configured as servers without displays such that the servers are controlled remotely via protocols such as HTTP or SSH.

While the local server 140 and the application data server 150 are illustrated as distinct servers in FIG. 1, in other examples these servers may be combined on one physical machine or the functionality may be distributed across multiple physical machines beyond those illustrated. For example, the functionality described for the local server 140 and the application data server 150 may be housed in one machine.

The communications network 170 can include local-area networks (LAN), wide-area networks (WAN), wireless networks (e.g., 802.11 or cellular network), the Public Switched Telephone Network (PSTN) network, ad hoc networks, personal area networks (e.g., Bluetooth) or other combinations or permutations of network protocols and network types. The network 170 may include a single local area network (LAN) or wide-area network (WAN), or combinations of LANs or WANs, such as the Internet. The various devices (e.g., first interactive device 110, second interactive device 120, local server 140, or application data server 150) coupled to the network 170 may be coupled to the communications network 170 via one or more wired or wireless connections.

In an example, the system 100 includes a massage specification system 160. The massage specification system 160 includes an input module 162, a process module 164, and a transmission module 166. The massage specification system 160 operates to collect preference input selections from a first user 180, process the preference inputs, and transmit a representation of the preference inputs to a second user 190 for display. The massage specification system 160 can be incorporated in the first interactive device 110, the second interactive device 120, the local server 140, or the application data server 150. In an example, the first interactive device 110 can have an application ("app") running on the first interactive device 110 to collect and process a set of preference inputs from a first user 180 for display of a representation of the set of preference inputs to the second user 190 via the second interactive device 120. In an example, the second interactive device 120 can incorporate the massage specification system 160 as an app running on the second interactive device 120 to collect and process the set of preference inputs from the first interactive device 110 and display a representation of the set of preference inputs to the second user 190 via the second interactive device 120. In an example, the first or second interactive devices 110, 120 can operate the massage specification system 160 by initiating an app to run on a separate computing machine, such as the local server 140, the application data server 150, or another remote computer accessed through the communications network 170.

The input module 162 operates to receive preference inputs from the first user 180 or the second user 190 through an interface. In an example, the interface is an electrical interface such as a GUI. In example, the interface is a mechanical interface such as the selection device 200. The input module 162 can transmit the preference inputs to the process module 164.

The process module 164 operates to process preference inputs for communication to the second user 190. In an example, the process module 164 can organize the preference inputs into a data structure, such as to form a set of preference inputs. In an example, the process module 164 can store preference inputs in a volatile computer memory for use in the transmission module 166. In an example, the process module 164 can save preference inputs in a non-volatile computer memory for future access. The process module 164 can transmit the preference inputs or the data structure to the transmission module 166.

In an example, the process module 164 can store one or more sets of preference inputs in a volatile computer memory for use in processing, calculating or generating additional preference inputs. For example, where the first user 180 defines a set of preference inputs and later changes one or more of the set of preference inputs to define an updated set of preference inputs, the process module 164 can compare the updated set of preference inputs to the set of preference inputs to identify changes made by the first user 180 to corresponding individual preference inputs. Each change to a corresponding individual preference input between a set of preference inputs and an updated set of preference inputs is a difference event. In an example, the numerical difference between corresponding individual values of a set of preference inputs and an updated set of preference inputs is a result of a difference event. For example, if a member of an updated set of preference inputs has a value greater than a corresponding member of a set of preference inputs, a positive difference event results. Similarly, if a member of an updated set of preference inputs has a value less than a corresponding member of a set of preference inputs, a negative difference event results. In an example, the result of a difference event can constitute a preference input. For example, the results of one or more difference events can be appended to the updated set of preference inputs as additional preference inputs.

After identifying one or more difference events, the process module 164 can generate an alert message to indicate a preference input has changed. In an example, the alert message is activated when the result of any of one or more difference events is identified. In an example, a unique alert message is generated for the result of each difference event identified. For example, when a first user 180 defines preference inputs of massage intensity and massage duration for a body zone (e.g., the set of preference inputs) and subsequently changes the massage intensity and massage duration for the body zone (e.g., the updated set of preference inputs), an alert message is generated for both the massage intensity difference event and the massage duration difference event. In an example, the alert message can constitute a preference input. For example, one or more alert messages can be appended to the updated set of preference inputs as additional preference inputs.

An alert message is a notice to the first user 180 and the second user 190 that a preference input or data structure has been modified or otherwise changed. In an example, after an alert message is displayed to the second user 190, the second user 190 can modify the delivery of the therapeutic massage to the first user 180. For example, modifying the delivery of the therapeutic massage to the first user 180 can include changing the body zone to which massage is applied, changing the massage intensity for the body zone or changing the massage duration.

The alert message is displayed to the first user 180, the second user 190 or both the first and second user 180, 190 through an interactive device, an interface or both an interactive device and an interface. The alert message is presented in a way that draws the attention of the first or second user 180, 190 to a change in the preference inputs. In an example, the alert message can display on the interactive device or the interface. In an example, the alert message can include, but is not limited to, the appearance of a static field of color on the GUI of an interactive device, a flashing field of color on the GUI of an interactive device, flashing text, or any combination of the aforementioned alert messages. For example, a positive difference event associated with a change in massage intensity can cause an intensity up alert region to activate. Similarly, a negative difference event can cause an intensity down alert region to activate. In an example, messages, music, sounds, or other audio outputs may accompany or be used in the place of the aforementioned alert messages. For example, the alert message can include, but is not limited to, a signal generation device (e.g., a speaker) connected to the interactive device that plays a sonic cue. For example, a sonic cue can be a soothing tone selected so as to notify the second user 190 but not to disturb the first user 180. In an example, electronic messaging is used to draw the attention of first or second user 180, 190. For example, the alert message can include, but is not limited to, the issuance of a text message or email.

The transmission module 166 operates to transmit a representation of the preference inputs or the data structure to the first user 180, the second user 190, or the first and second users 180, 190. In an example, the transmission module 166 can transmit a representation of the preference inputs, including alert messages, to a first interactive device 110, a second interactive device 120, or the first and second interactive devices 110, 120 for display to the respective users. In an example, the interface is an electrical interface such as a GUI.

Figure 3:
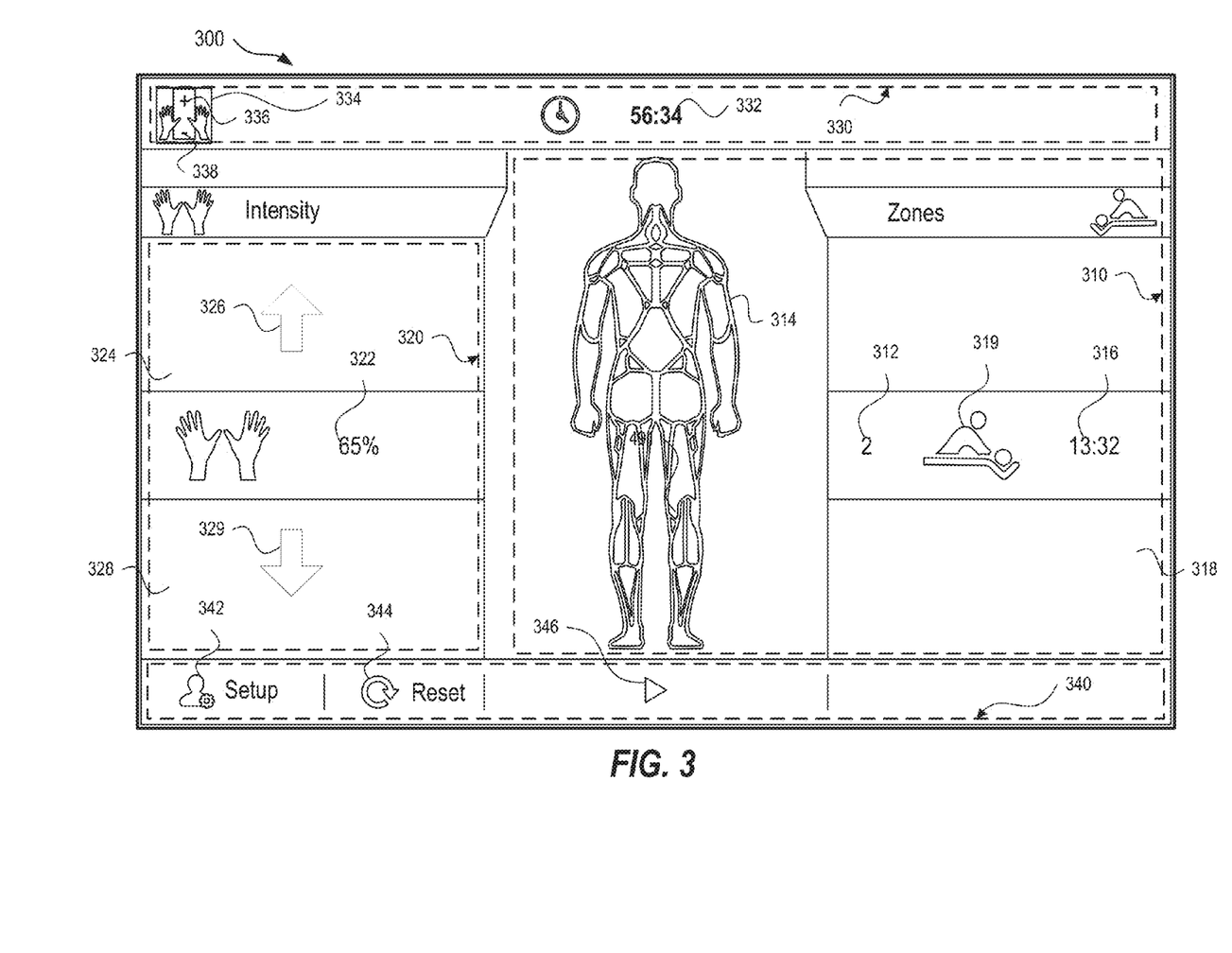
FIG. 3 is an example of a graphical user interface used for receiving and displaying preference inputs in connection with a therapeutic massage session.

FIG. 3 is an example of a graphical user interface (GUI display 300) used for receiving and displaying preference inputs in connection with a therapeutic massage. In an example, the GUI display 300 can be used to receive one or more preference inputs from a first user 180 and to display a representation of the preference inputs to a second user 190. The GUI display 300 can include a body zone section 310, an intensity section 320, a top information bar 330, and a bottom information bar 340.

The body zone section 310 can include a body zone number readout 312, a body zone graphic 314, a body zone timer 316, a body zone timer alert 318, and a body zone icon 319. In an example, the body zone number readout 312 can include indicia to designate different body zone preference inputs. In an example, the indicia can include, but is not limited to, numeric digits. For example, the number "1" can designate a first body zone such as muscle groups comprising the head and upper neck; the number "2" can designate a second body zone such as muscle groups comprising the lower neck, shoulders and arms; the number "3" can designate a third body zone such as muscle groups comprising the middle back; the number "4" can designate a fourth body zone such as muscle groups comprising the lower back and upper hips; the number "5" can designate a fifth body zone such as muscle groups comprising the buttocks and thighs; and the number "6" can designate a sixth body zone such as muscle groups comprising the shins and feet.

The body zone graphic 314 includes details of muscle groups to represent the human body. In an example, a specific body zone preference input corresponds to a portion of the body zone graphic 314. In an example, the body zone number readout 312 can correspond to a highlighted grouping of muscle groups in the body zone graphic 314 to pictorially represent the body zone to be massaged. For example, where the body zone number readout 312 displays the indicia "2" to indicate the second body zone to be massaged, the body zone graphic 314 highlights the corresponding muscle groups representing the second body zone (such as, the upper neck, shoulders and arms muscle groups) so as to provide a visual cue to the massage professional of the muscle groups to be massaged. In an example, as the body zone number readout 312 changes from a first body zone indicia to a second body zone indicia, the body zone graphic 314 can un-highlight the muscle groups representing the first body zone indicia and thereafter highlight the muscle groups representing the second body zone indicia. For example, where the body zone number readout 312 changes from the indicia "2" representing the second body zone to the indicia "3" representing the third body zone, the body zone graphic 314 can change from highlighting the upper neck, shoulders and arms representing the second body zone to highlighting the middle back representing the third body zone. In an example, the pairing of a corresponding body zone number readout 312 and body zone graphic 314 can be the same color for a given body zone. For example, the pairing of the body zone number readout 312 and the body zone graphic 314 can display both the indicia and the graphics for a given body zone in a single color to provide a visual cue to the second user 190 of the muscle groups to be massaged. In an example, each pairing of corresponding body zone number readout 312 and body zone graphic 314 can have a different color.

The body zone timer 316 displays the massage duration, or the allotted time of massage to be applied to a body zone. In an example, the first user 180 establishes the massage duration preference input for a body zone by specifying an amount of time in the body zone timer 316. In an example, the body zone timer 316 can act as a stopwatch to display the massage duration applied to the body zone. For example, upon toggling the pause-play control 346 (described below) to "play" mode, the body zone timer 316 can count up from zero to the massage duration or count down from the massage duration to zero. In an example, the body zone timer 316 can display the massage duration in different display formats. For example, the body zone timer 316 can display the massage duration in a minutes-only format, a seconds-only format, or a minutes and seconds format.

The body zone timer alert 318 notifies the first and second users 180, 190 that the massage duration for the body zone is complete or that a preference input associated with massage duration has changed. In an example, the body zone timer alert 318 can change from a blank field to a prominently colored field as the massage duration for the body zone is completed. In an example, the body zone timer alert 318 can notify the first and second users 180, 190 that the massage duration for the body zone is near completion. For example, when the massage duration for the body zone "2" is within 30 seconds of completion, the body zone timer alert 318 can change from a blank field to a prominently colored field to alert the massage professional that the massage duration is nearing completion. In an example the body zone timer alert 318 can be set to indicate the beginning of the allotted time of massage for the body zone. For example, when the massage duration for the body zone "2" has been completed and the massage duration for the body zone "3" is initiated, the body zone timer alert 318 can change from a blank field to a prominently colored field to alert the massage professional that the allotted time for massage is starting for the next body zone. In an example, the body zone timer alert 318 can be active for a period of time sufficient to alert the massage professional of the change in body zones massaged. For example, the body zone timer alert 318 can change from a blank field to a prominently colored field for approximately 30 seconds to alert the massage professional that the allotted time for massage is starting for the next body zone. In an example, the body zone timer alert 318 can include a sonic cue to alert the second user 190 that the preference inputs have been modified. For example, the sonic cue can include, but is not limited to, a tone, a chime, or a ringtone. In an example, the body zone timer alert 318 can issue a message-based cue to alert the second user 190 that the preference inputs have been modified. For example, the message-based cue can include, but is not limited to, activation of a service to generate a text message for receipt by an interactive device in vibration mode, such as a cell phone that is in close proximity to the second user 190.

The intensity section 320 can include an intensity readout 322, an intensity up alert region 324, and an intensity down alert region 328. In an example, the first user 180 establishes the massage intensity preference input for a body zone by specifying a massage intensity, which is represented in the intensity readout 322. In an example, the intensity readout 322 can include indicia to designate different massage intensity levels. For example, as shown in FIG. 3, the intensity readout 322 of "65%" can specify a relative massage intensity level to be applied to the second body zone (designated by the number "2" in the body zone number readout 312).

The intensity up alert region 324 can notify the second user 190 that the preference inputs have been modified to increase the intensity of massage as represented by the intensity number readout 322. In an example, the intensity up alert region 324 can notify the second user 190 by supplying a visual cue. For example, the visual cue can include changing the color of the intensity up alert region 324 from a first color to a second color or alternating between the first and second colors intermittently. In an example, the intensity up alert region 324 can include an icon 326 to supply an additional visual cue to the second user 190 that the preference inputs have been modified. For example, the icon 326 can include, but is not limited to, any symbol, such as an upwardly-pointing arrow that changes from a first color to a second color or alternates between the first and second colors intermittently. In an example, the intensity up alert region 324 can include a sonic cue to alert the second user 190 that the preference inputs have been modified. For example, the sonic cue can include, but is not limited to, a tone, a chime, or a ringtone.

The intensity down alert region 328 can notify the second user 190 that the preference inputs have been modified to decrease the intensity of massage as represented by the intensity number readout 322. In an example, the intensity down alert region 328 can notify the second user 190 by supplying a visual cue. For example, the visual cue can include changing the color of the intensity down alert region 328 from a first color to a second color or alternating between the first and second colors intermittently. In an example, the intensity down alert region 328 can include an icon 329 to supply an additional visual cue to the second user 190 that the preference inputs have been modified. For example, the icon 329 can include, but is not limited to, any symbol, such as a downwardly-pointing arrow that changes from a first color to a second color or alternates between the first and second colors intermittently. In an example, the intensity down alert region 328 can include a sonic cue to alert the second user 190 that the preference inputs have been modified. For example, the sonic cue can include, but is not limited to, a tone, a chime, or a ringtone.

The top information bar 330 can include a total massage time monitor 332 and an intensity control interface 334. The total massage time monitor 332 displays the sum of massage durations applied to individual body zones. In an example, the total massage time monitor 332 can count up from zero to the sum of massage durations to display the total amount of time spent in applying the therapeutic massage to a massage patient. In an example, the total massage time monitor 332 can count down from the sum of massage durations to zero to display the total amount of time remaining in a therapeutic massage session.

The intensity control interface 334 allows the massage patient to supply real-time preference information regarding the massage forces applied to the massage professional while a therapeutic massage is in progress. The intensity control interface 334 can include an intensity increase icon 336 and an intensity decrease icon 338 to adjust the intensity readout 322 from a first value to a second value. In an example, selection of the intensity up icon 336 or the intensity down icon 338 can adjust the intensity readout 322 by a predetermined quantity. For example, each selection instance of the intensity up icon 336 can increase the intensity readout 322 by a predetermined quantity, such as 1%, 5%, or 10%. Similarly, each selection instance of the intensity down icon 338 can decrease the intensity readout 322 by a predetermined quantity, such as 1%, 5%, or 10%.

The bottom information bar 340 can include a setup control 342, a reset control 344, and a pause-play control 346. In an example, the setup control 342 can initiate a setup control interface (not shown) that controls operation and display of the GUI display 300. For example, the setup control interface can display functions that include, but are not limited to, access to wireless connections, access to wireless devices, display brightness, and memory allocation.

The reset control 344 initiates a sequence of events to replay the therapeutic massage represented by the preference inputs. Where a therapeutic massage is halted for any reason, a massage professional can reinitiate the therapeutic by activating the reset control 344. In an example, the reset control 344 can initiate a sequence of events to replay a portion or the complete therapeutic massage represented by the preference inputs.

The pause-play control 346 operates as a switch to move between operational modes of the GUI display 300. In an example, the pause-play control 346 can operate as a toggle switch to toggle between a "play" mode represented by a triangular shaped indicia where a vertex of the triangular shaped indicia is pointing to the right of the GUI display 300 (shown in FIG. 3) and a "pause" mode represented by two parallel, vertically-oriented bars, otherwise generally known as a pause icon (not shown). In an example, the pause-play control 346 can manage the progression of the therapeutic massage. For example, when toggled to "play" mode, the body zone timer 316 can count up from zero to the massage duration whereas when toggled to "pause" mode, the body zone timer 316 can be temporarily suspended from counting.

Figure 4:
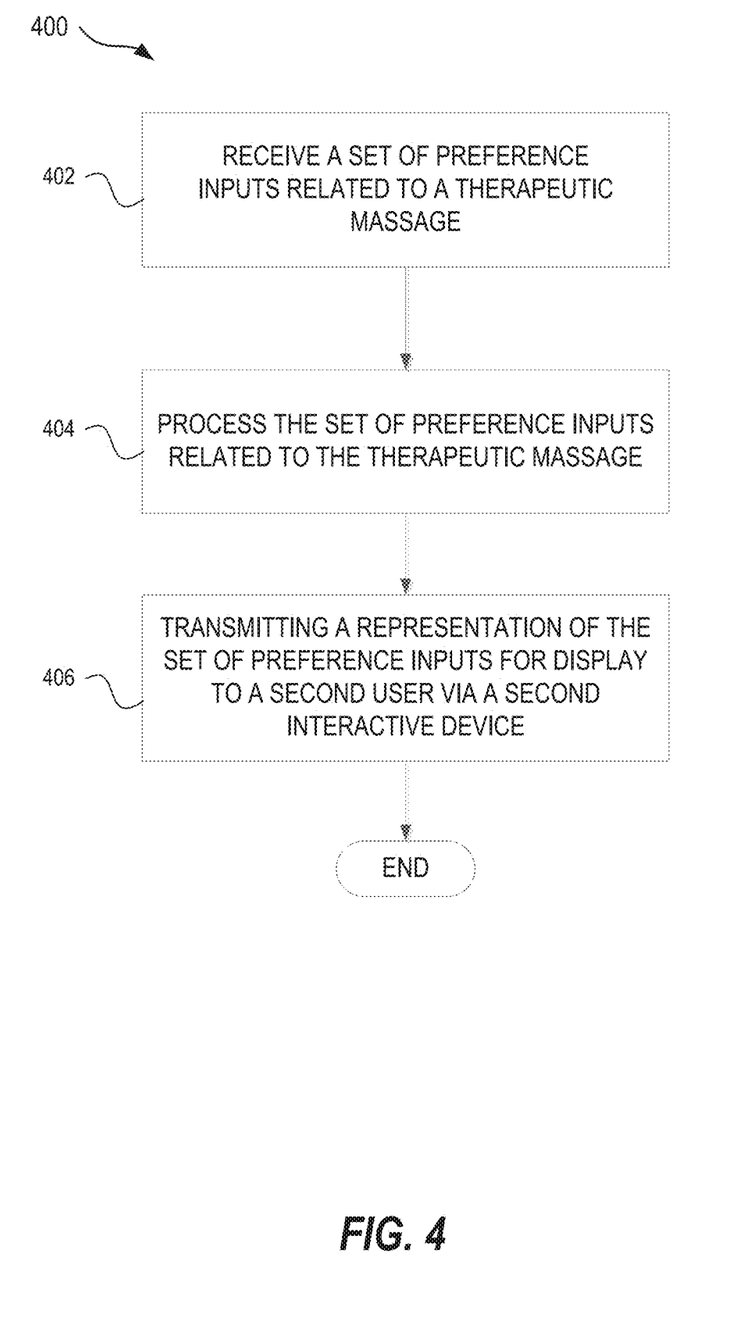
FIG. 4 is a flowchart of an example method for receiving preference inputs from a first user for display to a second user in connection with a therapeutic massage session according to an example.

FIG. 4 is a flowchart of an example method 400 for receiving preference inputs from a first user 180 for display to a second user 190 in connection with a therapeutic massage. At block 402, a set of preference inputs related to a therapeutic massage is received. In an example, a first interactive device 110 running an interface receives the set of preference inputs describing the therapeutic massage from the first user 180. In an example, the set of preference inputs describing the therapeutic massage can include primary preference inputs, such as body zones, and secondary preference inputs, such as massage intensity and massage duration.

At block 404, the set of preference inputs related to the therapeutic massage is processed. In an example, processing includes preparing the preference inputs for communication to a second user 190. In an example, processing includes organizing the preference inputs into a data structure. In an example, processing includes maintaining preference inputs in a volatile computer memory for use in the displaying and updating the preference inputs. In an example, processing includes saving preference inputs as a data structure to a computer memory for future access.

At block 406, a representation of the set of preference inputs is transmitted for display to the second user 190 via the second interactive device 120. In an example, the first interactive device 110 and a second interactive device 120 can display a representation of the set of preference inputs through an interface to the first and second users 180, 190 respectively. In an example, displaying the preference inputs includes a graphical, numerical, or combination of graphical and numerical representation of the preference inputs. For example, primary preference inputs, such as the body zone readout 312 and the body zone graphic 314, can be displayed as a combination of numerical and graphical representations, and secondary preference inputs, such as intensity readout 322 and body zone timer 316 can be displayed as numerical representations.

Figure 5:
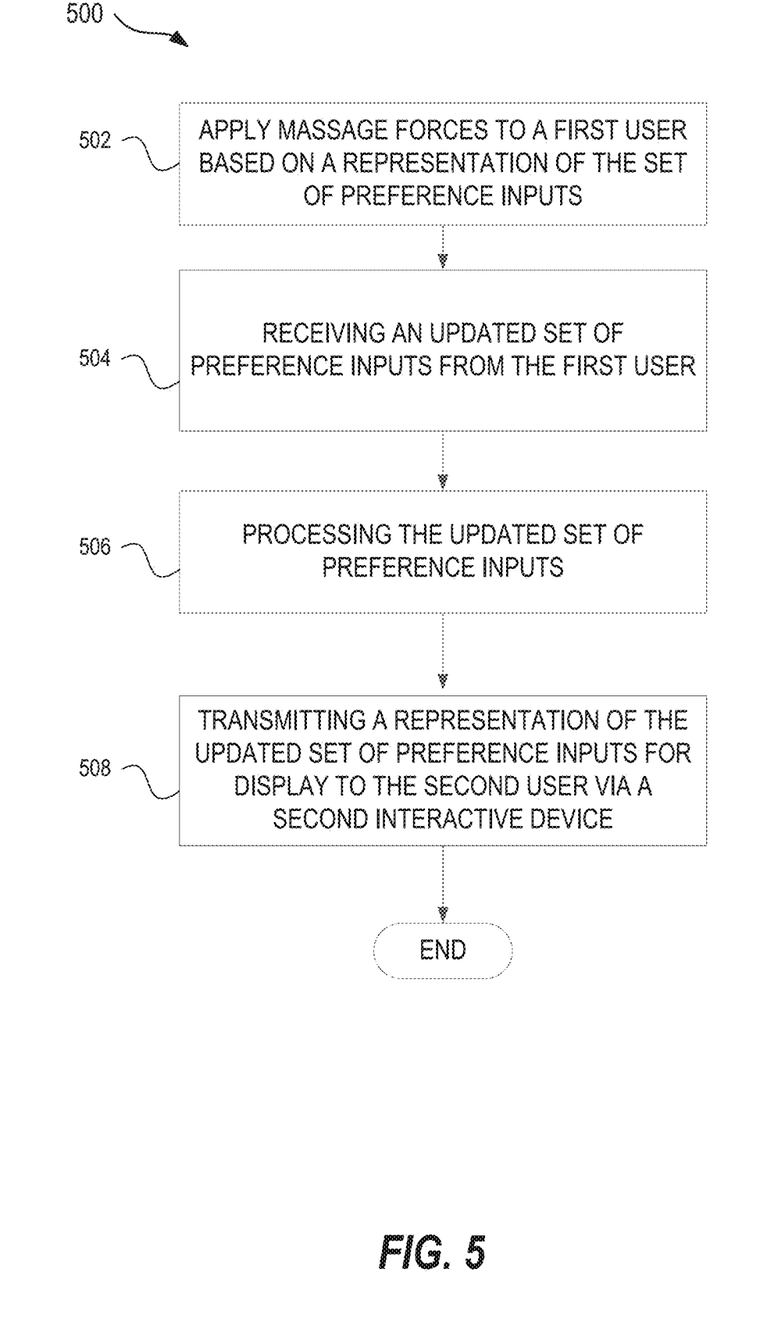
FIG. 5 is a flowchart for an example method of receiving an updated set of preference inputs from a first user for display to a second user in connection with a therapeutic massage session according to an example.

FIG. 5 is a flowchart of an example method 500 for receiving an updated set of preference inputs from a first user 180 for display to a second user 190 in connection with a therapeutic massage. At block 502, the second user 190 applies massage forces to the first user 180 based on the representation of the set of preference inputs. For example, where the representation of the preference inputs indicates a primary preference input, such as body zone "2" (e.g., the upper neck, shoulders, and arms) and secondary preference inputs, such as massage intensity "65" and massage duration of "13:52", the second user 190 applies therapeutic massage to the upper neck, shoulders and arms (e.g., body zone "2") of the first user 180 with a relatively intense massage (e.g., "65" in the range of "0" to "100") for a period of time (e.g., "13:52" corresponding to 13 minutes and 52 seconds of therapeutic massage). In response to the therapeutic massage applied by the second user 190, the first user 180 can perceive the applied massage forces and evaluate the suitability of the applied massage forces for the goals of the therapeutic massage. In an example, the first user 180 perceives the massage intensity of the applied massage forces, determines the suitability of the applied forces for the therapeutic massage, and thereafter modifies the set of preference inputs to form an updated set of preference inputs.

At block 504, an updated set of preference inputs is received from the first user 180, the updated set of preference inputs reflecting a modification to the massage being received by the first user 180. In an example, the updated set of preference inputs is in response to the application of massage forces by the second user 190 to the first user 180. For example, as the massage professional applies massage forces to the massage patient at the massage intensity specified by a first preference input and the massage patient perceives the massage intensity as insufficiently aggressive, the massage patient can modify the massage intensity specified by the first preference input to a updated preference input greater than the first preference input. In an example, the updated preference inputs can include primary preference inputs, such as body zones, and secondary preference inputs, such as massage intensity and massage duration. In an example, a first interactive device 110 running an interface receives the updated set of preference inputs describing the therapeutic massage from the first user 180.

At block 506, the updated set of preference inputs is processed. In an example, processing includes preparing the updated set of preference inputs for communication to a second user 190. In an example, processing includes organizing the updated set of preference inputs into a data structure. In an example, processing includes maintaining the updated set of preference inputs in a volatile computer memory for use in the displaying the updated set of preference inputs. In an example, processing includes saving the updated set of preference inputs as a data structure to a computer memory for future access. In an example, processing includes storing one or more sets of preference inputs in a volatile computer memory for use in processing, calculating or generating additional preference inputs. For example, the volatile computer memory can store the set of preference inputs and the updated set of preference inputs for use in generating alert messages.

At block 508, a representation of the updated set of preference inputs is transmitted to a second interactive device 120 for display to the second user 190 via the second interactive device 120. In an example, the representation of the updated preference inputs is displayed on the interface of the second interactive device 120.

Figure 6:
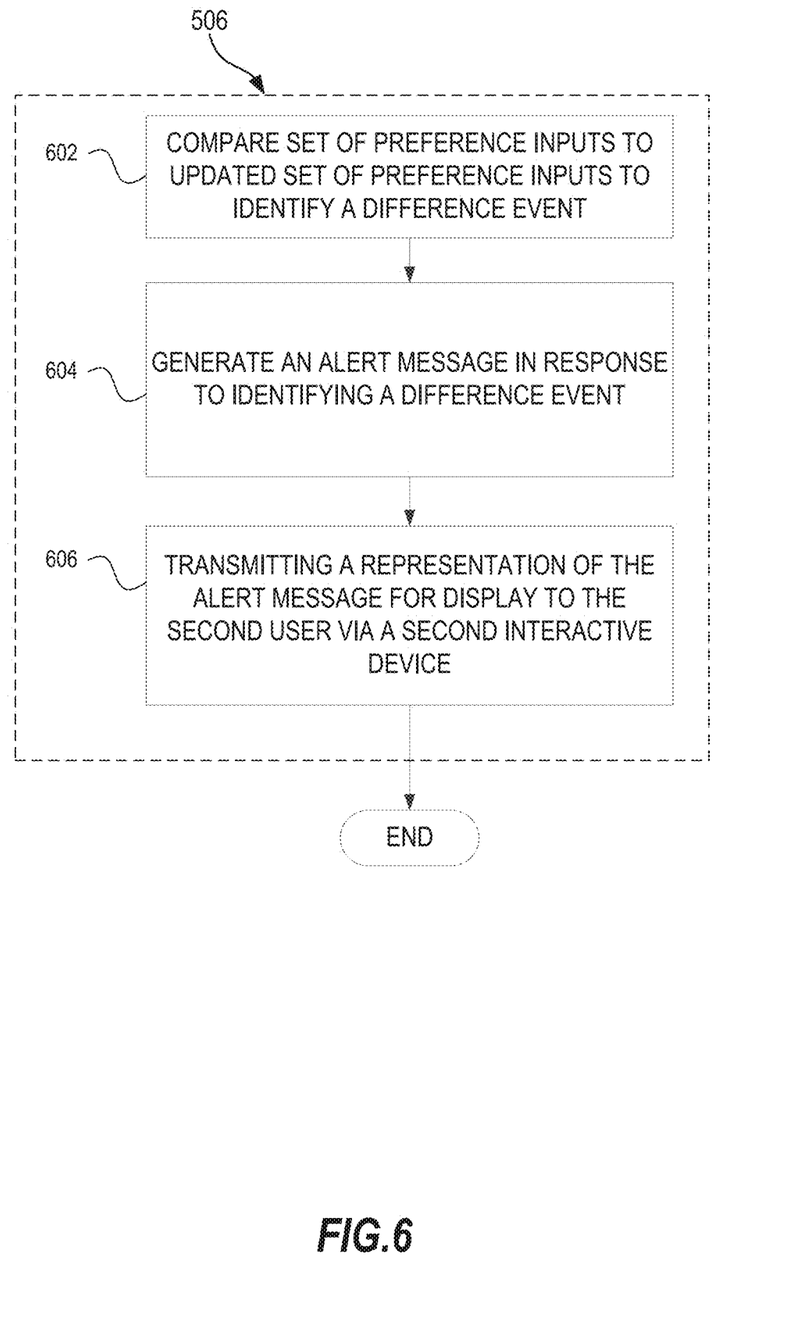
FIG. 6 is a flowchart of an example method to process the updated set of preference inputs.

FIG. 6 is a flowchart of an example method to process the updated set of preference inputs. In an example, block 506 can process the updated set of preference inputs to notify the first and second users 180, 190 of a change in the set of preference inputs in connection with a therapeutic massage. In an example, notification of the first and second users 180, 190 includes generation of an alert message. At block 602, the set of preference inputs is compared to the updated set of preference inputs to ascertain one or more difference events (e.g., differences between the set of preference inputs and the updated sets of preference inputs). In an example, the first and updated preference inputs sets are compared during processing. For example, the set of preference inputs and the updated set of preference inputs can be stored in volatile computer memory and compared to identify difference events.

At block 604, an alert message is generated in response to the presence of a difference event. In an example, one or more alert messages can be created in response to the presence of one or more difference events.

At block 606, a representation of the alert message is transmitted for display to the second user 190 via the second interactive device 120. In an example, the alert message is displayed to the first and second users. For example, the alert message can be displayed on the first interactive device 110, the second interactive device 120, or both the first and second interactive devices 110, 120. In an example, the result of the difference event can influence the alert message displayed. For example, where the first user 180 creates a updated preference input set by increasing the preference input for massage intensity, the result of the difference event is a positive number resulting in an alert message that causes the intensity up alert region 324 to display. In an example, the alert message is appended to the updated set of preference inputs for transmission to the second user 190.

Although the preceding examples were provided with specific reference to uses of massage therapy in massage therapy settings, it will be apparent that further application of the techniques and configurations described herein will apply to a variety of settings such as: physical or rehabilitative therapy, chiropractic therapy, exercise training, and a variety of other medical or coaching settings. Further, the various software applications and devices used to collect and output preference inputs may have applicability to a variety of use cases.

Operating devices such as the first interactive device 110, the second interactive device 120, the local server 140, and the application data server 150 may be electronic devices that can include a processor, a memory, one or more applications stored on memory, a display, an input interface and a network interface. In an example, the processor can execute instructions stored on the memory to affect the functionality described herein. An input interface can include, but is not limited to, a keyboard, a stylus, a touchscreen, voice-control interfaces or gesture-interpreting interfaces. A network interface can include, but is not limited to, hardware and software to enable transmission of data over wired communication pathways, such as Ethernet or USB, or wireless communication protocols such as GSM, CDMA, Wi-Fi, LTE, or the like.

In some examples, the first interactive device 110, the second interactive device 120, the local server 140, and the application data server 150 are computing devices. For example, a computing device can include, but is not limited to, a personal computer, a tablet computer, or a smart-phone. The local server 140 and the application data server 150 can be configured as computing devices that operate as servers for various other computing devices (e.g., client devices). For example, a server can include, but is not limited to, any computing device that can be remotely controlled or interacted with HTTP or SSH protocols.

The therapeutic massage communication application software can operate from various hardware platforms. In an example, the application data server 150 can store the therapeutic massage communication application software for remote execution by users. In a first example, the first user 180 with first device 110 can connect to the communications network 170 and thereby gain access to the application data server 150 on which the therapeutic massage communication application software can be initiated. In a second example, the first user 180 with first device 110 can connect to the local server 140 so as to provide centralized data protection and thereafter connect to the communications network 170 to gain access to the application data server 150 on which the therapeutic massage communication application software can be initiated.

Preference input information can be stored on different hardware platforms. In an example, preference inputs can be stored on a computing device. For example, preference inputs contained in a data file can be located in the memory of a mobile electronic device such as first interactive device 110 or second interactive device 120 or a personal computer such as local server 140. In an example, preference inputs can be stored on a server. For example, preference inputs contained in a data file can be located in the memory of a personal computer such as application data server 150 with access to other computing devices through the communications network 170. Other variations of the previously described electronic device configurations may be provided to implement the techniques described herein.

Figure 7:
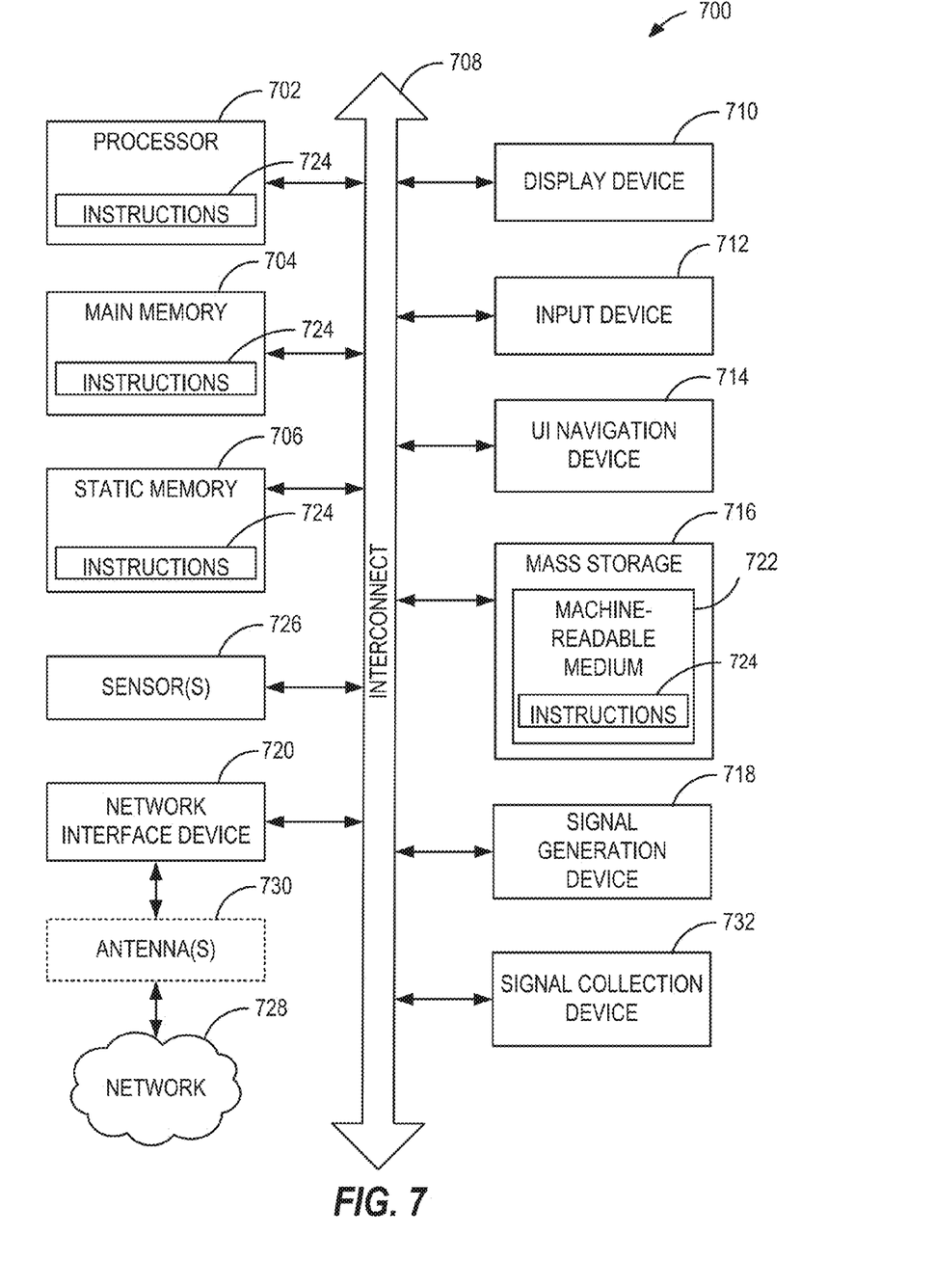
FIG. 7 is a schematic representation of a computing machine.

FIG. 7 is a schematic representation of a computing machine 700 wherein a set of instructions that can cause the computing machine 700 to execute any one or more of the processes, methods or operations described in this disclosure may be performed. For example, the computing machine 700 can be a computer, such as a personal computer (or PC), tablet PC, a personal digital assistant (PDA), a mobile (or cellular) telephone, a web appliance, or any other machine that can execute a set of instructions of actions to be taken by the machine. In an example, the machine can function as a stand-alone device or can be integrated, or otherwise connected, into a network of other machines. For example, when operating in a network, the computing machine 700 can function as a server or a client machine in server-client network environments or as a peer machine in a peer-to-peer network. As used herein, the terms computing machine or computing device can include any network or collection of machines that can individually or in combination execute a set or multiple sets of instructions to perform a function recited in this disclosure.

In an example, the computing machine 700 can include a processor 702 with at least one central processing unit (CPU), at least one graphics processing unit (GPU) or at least one of both a CPU and a GPU, a main memory 704, a static memory 706 and an interconnect (e.g., bus) 708 through which each of the aforementioned components can communicate with one another. In an example, the computing machine 700 can also include a video display device 710, an input device 712 (e.g., a keyboard alphanumeric input device), a user interface navigation device 714 (e.g., a touchscreen sensor, a button array, a trackpad, or a mouse). The computer system 700 may additionally include a storage device 716 (e.g., a drive unit), a signal generation device 718 (e.g., a speaker), a signal collection device 732 (e.g., a camera or a microphone), a network interface device 720 (which may include or operably communicate with one or more antennas 730, transceivers, or other wireless communications hardware), and one or more sensors 726, such as a global positioning system (GPS) sensor, compass, accelerometer, location sensor, or other sensor.

The storage device 716 includes a machine-readable medium 722 on which is stored one or more sets of data structures and instructions 724 (e.g., software) embodying or utilized by any one or more of the methodologies or functions described herein. The instructions 724 may also reside, completely or at least partially, within the main memory 704, static memory 706, and/or within the processor 702 during execution thereof by the computer system 700, with the main memory 704, static memory 706, and the processor 702 also constituting machine-readable media.

While the machine-readable medium 722 is illustrated in an example embodiment to be a single medium, the term "machine-readable medium" may include a single medium or multiple media (e.g., a centralized or distributed database, and/or associated caches and servers) that store the one or more instructions 724. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 724 may further be transmitted or received over a communications network 728 using a transmission medium via the network interface device 720 utilizing any one of a number of well-known transfer protocols (e.g., HTTP). Examples of communication networks include a local area network (LAN), a wide area network (WAN), the Internet, mobile telephone networks, and wireless data networks (e.g., Wi-Fi, 2G/3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Additional examples of the presently described method, system, and device embodiments include the configurations recited by the claims. Each of the examples in the claims may stand on its own, or may be combined in any permutation or combination with any one or more of the other examples provided below or throughout the present disclosure.

What is claimed is:

1. A method for conveying massage preferences of a first user to a second user, the first user receiving a massage from the second user, the massage described by a set of preference inputs, the method comprising:
   receiving at a first interactive device, an updated set of preference inputs from the first user, the updated set of preference inputs reflecting a modification to the massage being received by the first user;
   processing the updated set of preference inputs, wherein processing the updated set of preference inputs includes comparing the set of preference inputs to the set of updated preference inputs to identify a difference event; and
   transmitting a representation of the updated set of preference inputs for display to the second user via a second interactive device.

2. The method of claim 1, wherein receiving the updated set of preference inputs at the first interactive device includes updating the set of preference inputs through a selection device.

3. The method of claim 1, wherein the modification to the massage being received by the first user arises from physiological stimulation of the first user in response to massage forces applied by the second user.

4. The method of claim 1, wherein processing the updated set of preference inputs further includes generating an alert message in response to the difference event.

5. The method of claim 4, wherein processing the updated set of preference inputs further includes appending alert messages to the updated set of preference inputs.

6. The method of claim 1, comprising:
   displaying the set of preference inputs.

7. A method for conveying massage preferences of a first user to a second user, the first user receiving a massage from the second user, the massage described by a set of preference inputs, the method comprising:
   receiving at a first interactive device, an updated set of preference inputs from the first user, the updated set of preference inputs reflecting a modification to the massage being received by the first user;
   processing the updated set of preference inputs;
   transmitting a representation of the updated set of preference inputs for display to the second user via a second interactive device; and
   displaying the set of preference inputs in a first color,
   wherein transmitting the representation of the updated set of preference inputs for display to the second user via the second interactive device comprises transmitting the representation of the updated set of preference inputs for display in a second color different that the first color.

8. The method of claim 7, wherein displaying the representation of the updated set of preference inputs includes displaying a body zone preference input and a corresponding portion of a body zone graphic.

9. The method of claim 7, wherein displaying the representation of the updated set of preference inputs includes displaying an alert message in response to a difference event.

10. The method of claim 9 wherein displaying an alert message includes activating an intensity up alert region in response to a positive difference event between a corresponding massage intensity preference input and updated massage intensity preference input.

11. The method of claim 9 wherein displaying an alert message includes activating an intensity down alert region in response to a negative difference event between a corresponding massage intensity preference input and updated massage intensity preference input.

12. The method of claim 9, wherein displaying an alert message includes generating a sonic cue.

13. The method of claim 9, wherein displaying an alert message includes activation of a service to generate a text message for receipt by an interactive device in vibration mode.

14. A computer-readable medium comprising instructions for conveying massage preferences of a first user to a second user, the first user receiving a massage from the second user, the massage described by a set of preference inputs, where the instructions when executed by a computer, cause the computer to:
   receive at a first interactive device, an updated set of preference inputs from the first user, the updated set of preference inputs reflecting a modification to the massage being received by the first user;
   process the updated set of preference inputs, wherein processing the updated set of preference inputs includes comparing the set of preference inputs to the set of updated preference inputs to identify a difference event; and transmit a representation of the updated set of preference inputs for display to the second user via an interactive device.

15. The computer-readable medium of claim 14, wherein the instructions to process the updated set of preference inputs include instructions to generate an alert message in response to the difference event.

16. A computer-readable medium comprising instructions for conveying massage preferences of a first user to a second user, the first user receiving a massage from the second user, the massage described by a set of preference inputs, where the instructions when executed by a computer, cause the computer to:

receive at a first interactive device, an updated set of preference inputs from the first user, the updated set of preference inputs reflecting a modification to the massage being received by the first user;

process the updated set of preference inputs;

transmit a representation of the updated set of preference inputs for display to the second user via an interactive device; and display the set of preference inputs in a first color, wherein the instructions to transmit the representation of the updated set of preference inputs for display to the second user via the second interactive device comprise instructions to transmit the representation of the updated set of preference inputs for display in a second color different that the first color.

17. The computer-readable medium of claim 16, wherein the instructions to display the representation of the updated set of preference inputs include instructions to display a body zone preference input and a corresponding portion of a body zone graphic.

* * * * *